United States Patent
Szasz et al.

(10) Patent No.: US 11,241,594 B2
(45) Date of Patent: Feb. 8, 2022

(54) FACE MASK FOR FILTERING AIR AND AIR MONITORING SYSTEM

(71) Applicant: CANADA PROSPER APPAREL LTD., Kitchener (CA)

(72) Inventors: Richard Devin Szasz, Waterloo (CA); Brandon James Leonard, Wellesley (CA); Peter Lionel Whitby, Waterloo (CA); Steven Henry Fyke, Waterloo (CA); Michael Joseph Defazio, Waterloo (CA); Jason Tyler Griffin, Kitchener (CA)

(73) Assignee: O2 INDUSTRIES INC., Kitchener (CA)

(*) Notice: Subject to any disclaimer, the term of this patent is extended or adjusted under 35 U.S.C. 154(b) by 342 days.

(21) Appl. No.: 16/331,675

(22) PCT Filed: Sep. 5, 2017

(86) PCT No.: PCT/CA2017/051039
§ 371 (c)(1),
(2) Date: Mar. 8, 2019

(87) PCT Pub. No.: WO2018/045456
PCT Pub. Date: Mar. 15, 2018

(65) Prior Publication Data
US 2019/0358473 A1  Nov. 28, 2019

Related U.S. Application Data

(60) Provisional application No. 62/393,266, filed on Sep. 12, 2016.

(51) Int. Cl.
*A62B 9/00* (2006.01)
*A62B 18/08* (2006.01)
(Continued)

(52) U.S. Cl.
CPC .............. *A62B 9/006* (2013.01); *A62B 18/08* (2013.01); *A62B 18/10* (2013.01); *A62B 23/025* (2013.01);
(Continued)

(58) Field of Classification Search
CPC ......... A62B 9/006; A62B 18/08; A62B 18/10; A62B 23/025; G01N 33/0031; G01N 33/0063; G08B 5/38; G08B 21/182
See application file for complete search history.

(56) References Cited

U.S. PATENT DOCUMENTS 2,787,333 A  4/1957  Boone et al.
3,028,602 A  4/1962  Miller
(Continued)

FOREIGN PATENT DOCUMENTS

CN  1707464 A  12/2005
CN  201036668 Y  3/2008
(Continued)

OTHER PUBLICATIONS

English machine translation of CN205041998U, published on Feb. 24, 2016.
(Continued)

*Primary Examiner* — Hongmin Fan
(74) *Attorney, Agent, or Firm* — Perry + Currier

(57) ABSTRACT

A face mask for filtering air includes a face seal for providing an airtight flexible seal around the nose and mouth of a user, a support sealably attached to the face seal, wherein the support has an open area that allows for passage of incoming air and outlet valves for expelling exhaled air, a front shell for removably attaching to the support, wherein the front shell has inlet holes for allowing the incoming air to pass through the open area of the support, and a filter for filtering particulate elements from air. The filter is configured to be
(Continued)

housed between the front shell and the support. The face seal provides a direct connection between the filter and the user.

15 Claims, 15 Drawing Sheets

(51) Int. Cl.
    *A62B 18/10*         (2006.01)
    *A62B 23/02*         (2006.01)
    *G01N 33/00*         (2006.01)
    *G08B 5/38*          (2006.01)
    *G08B 21/18*         (2006.01)

(52) U.S. Cl.
    CPC ..... *G01N 33/0031* (2013.01); *G01N 33/0063* (2013.01); *G08B 5/38* (2013.01); *G08B 21/182* (2013.01)

(56) References Cited

U.S. PATENT DOCUMENTS

| | | | |
|---|---|---|---|
| 4,630,604 A | 12/1986 | Montesi | |
| 4,942,628 A | 7/1990 | Freund | |
| 5,499,624 A * | 3/1996 | Kruger | A62B 9/025 128/204.26 |
| 5,924,420 A | 7/1999 | Reischel et al. | |
| 5,950,245 A | 9/1999 | Binduga | |
| 6,062,221 A | 5/2000 | Brostrom et al. | |
| 6,497,232 B2 | 12/2002 | Fecteau et al. | |
| 6,536,435 B1 | 3/2003 | Fecteau et al. | |
| 6,817,362 B2 | 11/2004 | Gélinas et al. | |
| 7,527,057 B2 | 5/2009 | Fecteau et al. | |
| 8,574,331 B2 | 11/2013 | Bangera | |
| 8,839,788 B2 | 9/2014 | Betz et al. | |
| 2002/0092525 A1 | 7/2002 | Rump et al. | |
| 2003/0029454 A1* | 2/2003 | Gelinas | A62B 23/025 128/205.27 |
| 2007/0277829 A1 | 12/2007 | Casewell | |
| 2009/0065006 A1* | 3/2009 | Patterson | A62B 18/025 128/205.27 |
| 2013/0104733 A1* | 5/2013 | Bangera | A62B 23/025 95/8 |
| 2013/0340768 A1 | 12/2013 | Gebrewold et al. | |
| 2015/0053206 A1 | 2/2015 | Seppälä et al. | |
| 2016/0213957 A1* | 7/2016 | Xu | A62B 18/025 |

FOREIGN PATENT DOCUMENTS

| | | |
|---|---|---|
| CN | 203954488 U | 11/2014 |
| CN | 104548405 A | 4/2015 |
| CN | 204635135 U | 9/2015 |
| CN | 205041998 U | 2/2016 |
| EP | 2609966 A1 | 7/2013 |
| KR | 1020060039128 A | 5/2006 |
| KR | 1020160002280 A | 1/2016 |
| WO | 2010064862 A2 | 6/2010 |
| WO | 2013063350 A1 | 5/2013 |
| WO | 2016188039 A1 | 12/2016 |
| WO | 2017136336 A1 | 8/2017 |

OTHER PUBLICATIONS

English machine translation of CN203954488U, published on Nov. 26, 2014.
English machine translation of KR1020060039128A, published on May 8, 2006.
English machine translation of WO2010064862A9, published on Jun. 10, 2010.
International Preliminary Report on Patentability dated Mar. 12, 2019 in related International Patent Application No. PCT/CA2017/051039 (7 pages).
Supplementary Partial European Search Report dated May 26, 2020 in related EP Patent Application No. 17847844.2 (15 pages).
English machine translation of CN201036668Y, published on Mar. 19, 2008.
English machine translation of CN1707464A, published on Dec. 14, 2005.
Extended European Search Report dated Sep. 9, 2020 in related EP Patent Application No. 17847844.2 (50 pages).
Office Action dated Apr. 7, 2021 in related Chinese Patent Application No. 201780062101.3 (8 pages).
Common knowledge reference cited in related Chinese Patent Application No. 201780062101.3 (3 pages).

* cited by examiner

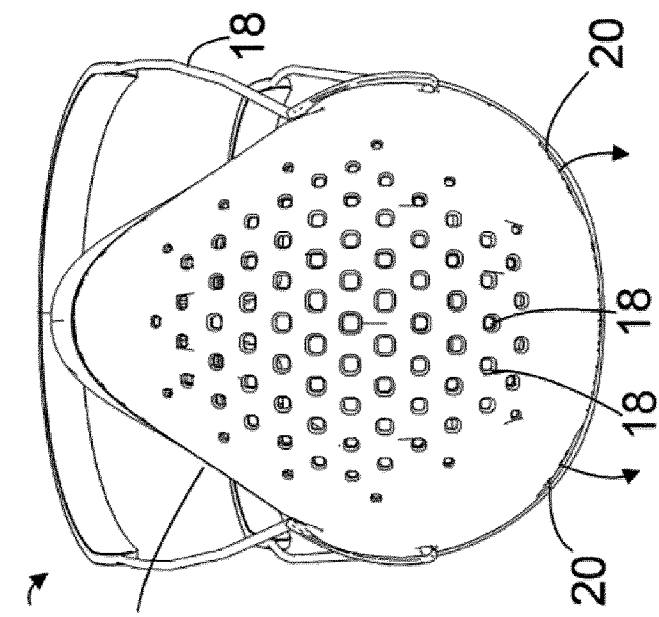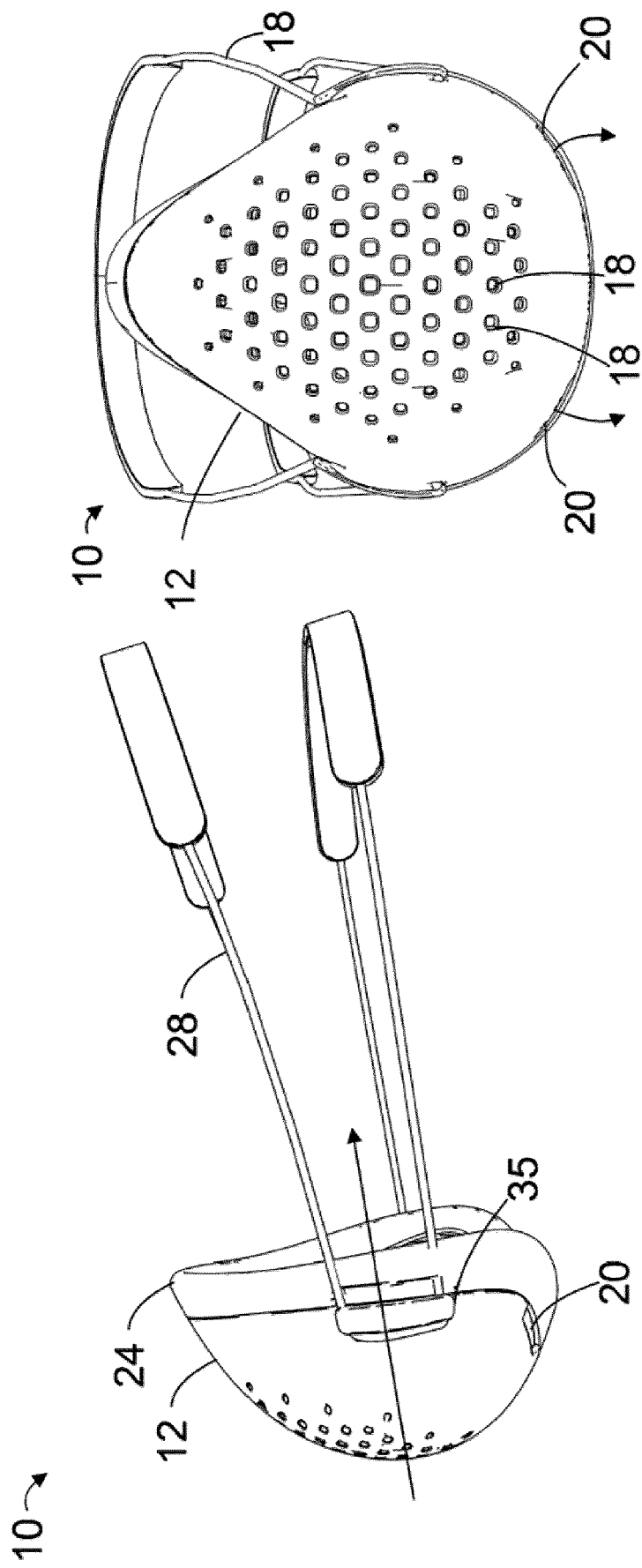

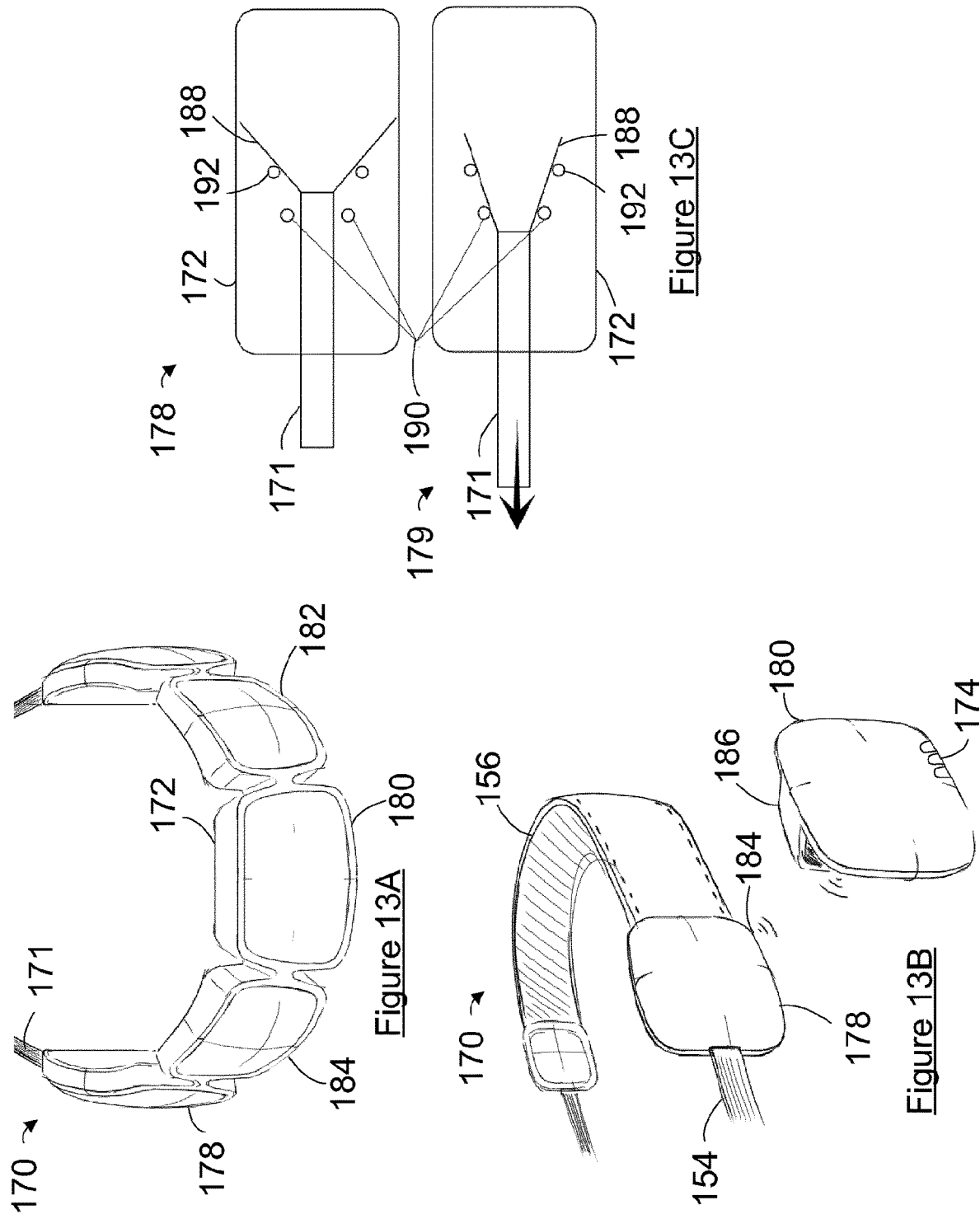

FACE MASK FOR FILTERING AIR AND AIR MONITORING SYSTEM

TECHNICAL FIELD

The embodiments disclosed herein relate to respirators and air monitoring systems, and, in particular to face masks for filtering air and systems for monitoring air quality.

INTRODUCTION

Respiratory masks are used in a wide variety of applications to protect a human's respiratory system from particles suspended in the air or from unpleasant or noxious gases. They are also frequently worn by, for example, medical care providers to prevent the spread of harmful micro-organisms either to or from the user.

Persons who work in polluted environments commonly wear filtering face masks to protect themselves from inhaling airborne contaminants. Filtering face masks typically have a fibrous or sorbent filter that is capable of removing particulate and/or gaseous contaminants from the air.

Respiratory masks have a variety of uses, including protecting a user from harmful bacteria or particles contained within unfiltered air. Existing respirators may not account for situations in which the filter degrades due to the pollutants filtered by the filter. These filtered pollutants cause the filter to degrade, requiring that the user receive filtered air through a degraded filter. This may require the replacement of the respiratory mask.

SUMMARY

According to some embodiments, there is provided a face mask for filtering air. The face mask includes a face seal for providing an airtight flexible seal around the nose and mouth of a user, a support sealably attached to the face seal, wherein the support has an open area that allows for passage of incoming air and outlet valves for expelling exhaled air, a front shell for removably attaching to the support, wherein the front shell has inlet holes for allowing the incoming air to pass through the open area of the support, and a filter for filtering particulate elements from air, wherein the filter is configured to be housed between the front shell and the support.

According to some embodiments there is provided a face mask for filtering air. The face mask includes a face seal for providing an airtight flexible seal around the nose and mouth of a user, a support sealably attached to the face seal, wherein the support has an open area that allows for passage of incoming air and outlet valves for expelling exhaled air, a front shell for removably attaching to the support, wherein the front shell has inlet holes for allowing the incoming air to pass through the open area of the support, and a filter for filtering particulate elements from air, wherein the filter is configured to be housed between the front shell and the support, and the face seal provides a direct connection between the filter and the user.

The support may include a framework that defines the open area. The framework may include a central longitudinal frame member and at least two transverse frame members.

The front shell may include a pair of shell attachment members located at a sides of the front shell. The support may include a pair of inner attachment members that removably connect to the shell attachment members.

The front shell may include a top shell connector located at a nose position of the front shell. The support may include an upper attachment member that hingedly connects with the top shell connector.

The shell attachment members may include an external release for disengaging the shell attachment member from the inner attachment member and thereby opening the face mask like a clam shell.

The face seal may be made of silicone. The face seal may be overmolded to the support such that the face seal seals the perimeter of the filter between the support and the front shell.

The filter may be configured to be flat when not assembled and be curved to become a three dimensional form for insertion on to the support.

The filter may include a pair of nose portions separated by a central nose slit. The nose portions mate together to form the three dimensional form when the filter is housed between the front shell and the support.

The face seal may include a nose seal extending along a central longitudinal frame member of the support. The nose seal may include a connector post connected to a post hole in the central longitudinal frame member. The nose seal is positioned to seal the nose portions of the filter to provide an airtight seal between the filter and the support.

The front shell may include filter registration members located on an inside surface of the front shell for aligning the filter within the face mask.

The front shell may include a number of stand-offs on an inside surface of the front shell adjacent to the inlet holes, for holding the filter off of the inner surface of the front shell.

The face mask may further include a head strap attached to the front shell or the support for holding the face mask to a user's face.

The face mask may further include a pollution sensor mounted to the head strap for monitoring the amount of particulate in the air. The head strap may include a communication system for communicating with the pollution sensor and a user communication device. The pollution sensor may include a tension switch having a spring loaded in tension that turns the pollution sensor on when the face mask is on the user's head.

According to some embodiments there is provided an air monitoring system. The air monitoring system includes a face mask for filtering air, a mask sensor device, and a user communication device in communication with the mask sensor device for receiving air quality readings (AQRs) from the mask sensor device, wherein the user communication device displays air quality data based on the AQRs received from the mask sensor device. The mask sensor device includes at least one pollution sensor for taking AQRs, and a pollution circuit having a memory for storing the AQRs, a processor for processing the AQRs, a transceiver for sending and receiving the AQRs, and a power supply for supplying power to the pollution circuit.

The mask sensor device may be mounted externally to the face mask.

The mask sensor device and the user communication device may communicate with a server via a network. The server determines an AQR accuracy based on the proximity, distance, time, and predictability of existing AQRs. If the AQR accuracy is above a predetermined threshold the air quality data is displayed on the user communication device. If the AQR accuracy is below the predetermined threshold, the mask sensor device performs a new pollution measurement and sends the AQR to the server.

In certain cases, when the user communication device identifies a change of environment, the at least one pollution sensor takes a new AQR.

The user communication device may include a filter life module that determines any one or more of filter life, filter effectiveness, and lifetime usage based of off the user's breathing rate or airflow, the duration of time the user has worn the face mask, and the levels of air pollutants during that time at the user's location from the AQR data.

The mask sensor device may include a light controlled by the pollution circuit, and wherein the light flashes if AQRs reach a predetermined upper or lower threshold.

The system may include at least two mask sensor devices in close proximity. A first mask sensor device provides AQRs to a second mask sensor device.

The face mask of the system may include a face seal for providing an airtight flexible seal around the nose and mouth of a user, a support sealably attached to the face seal, wherein the support has an open area that allows for passage of incoming air and outlet valves for expelling exhaled air, a front shell for removably attaching to the support, wherein the front shell has inlet holes for allowing the incoming air to pass through the open area of the support, and a filter for filtering particulate elements from air, wherein the filter is configured to be housed between the inlet holes of the front shell and the open area of the support and the face seal provides a direct connection between the filter and the user.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatus of the present specification. In the drawings:

FIG. 2 is a side view of the face mask of FIG. 1;

FIG. 3 is a front view of the face mask of FIG. 1;

FIGS. 13A and 13B are perspective views of a head strap and pollution sensor a face mask, in accordance with further embodiments;

FIG. 13C is a schematic drawing of a tension switch of a head strap, in accordance with an embodiment;

DETAILED DESCRIPTION

Figure 1:
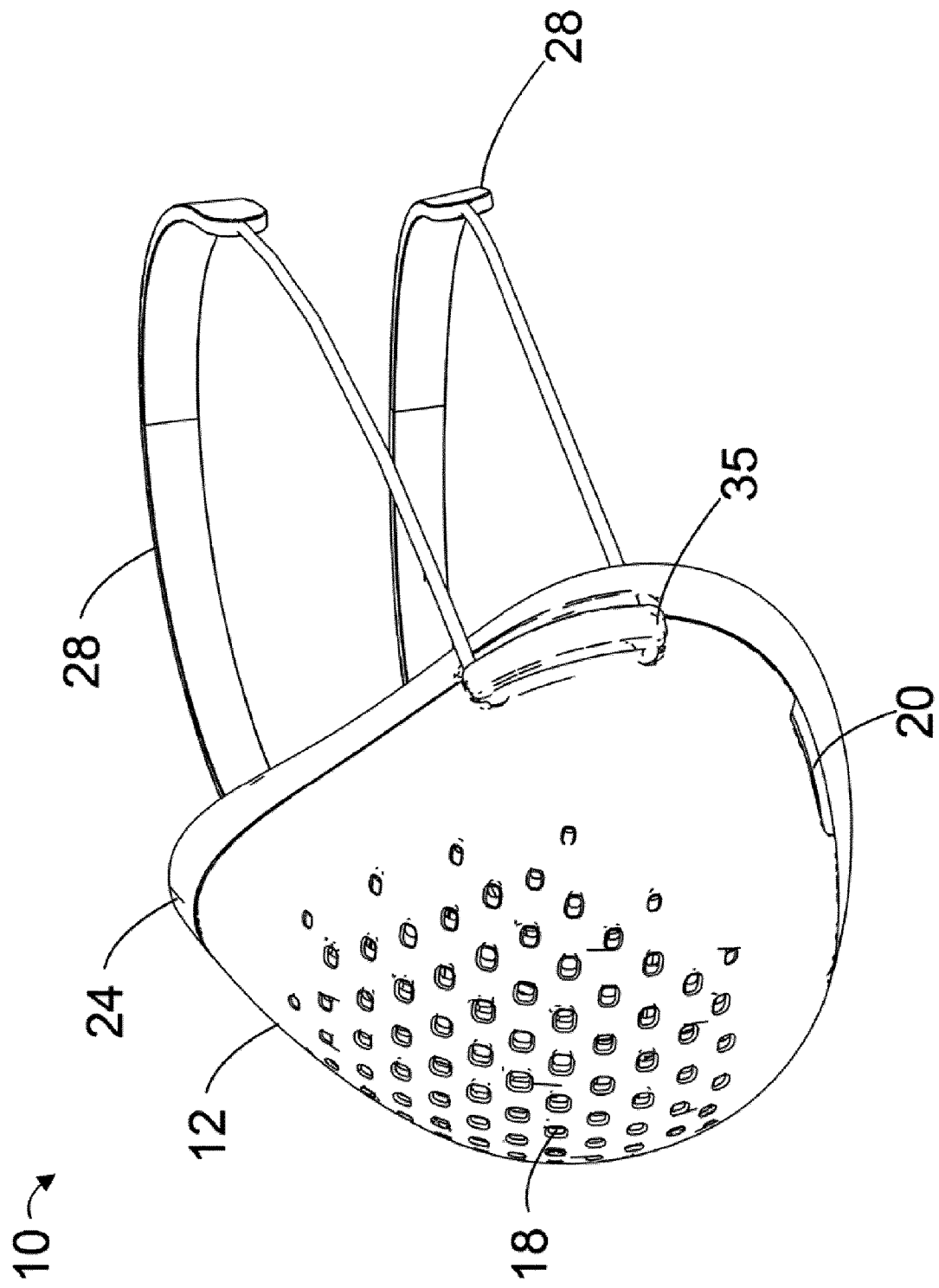
FIG. 1 is a perspective view of a face mask, according to one embodiment.

Various apparatus or processes will be described below to provide an example of each claimed embodiment. No embodiment described below limits any claimed embodiment and any claimed embodiment may cover processes or apparatuses that differ from those described below. The claimed embodiments are not limited to apparatuses or processes having all of the features of any one apparatus or process described below or to features common to multiple or all of the apparatuses described below.

Referring to FIGS. 1 to 5, illustrated therein is a face mask 10 for filtering air. More particularly, the face mask 10 is a respiratory mask for filtering pollutants and particulate based airborne contaminants from the air when positioned over the face of a user. Air is drawn in by the user's breath and pollutants are filtered out and prevented from entering the respiratory system of the user. As the user exhales, the face mask 10 expels the exhaled air. The face mask 10 includes components that may provide ease of manufacture and simple assembly and replacement of parts for the user. Pollutants and airborne contaminants filtered may include carbon monoxide, nitrogen oxides, ozone, sulphur, PM2.5, PM10, and pollen. Pollen from plants may be filtered by the face mask 10 to prevent allergies and reactions in humans.

The face mask 10 includes a front shell 12 that acts as an outer layer of the face mask 10 and provides a protective outer surface. The front shell 12 attaches to a support 16 and the front shell 12 and the support 16 work together to hold a filter 14 therebetween. The support 16 provides structure to and supports the filter 14 in the face mask 10 while the front shell 12 protects the filter 14 and inner components of the face mask 10.

The front shell 12 may be made of rigid, semi-rigid, or flexible material such as thermoplastic, carbon fiber, and plastic. The front shell 12 may also include an aesthetic layer made of materials such as gold, platinum, and flexible materials such as lace, leather, fabrics, and silk. In certain embodiments, the front shell 12 may be attached to various clothing-type garments, such as, scarfs, jackets, balaclavas, sweaters, and helmets. The front shell 12 may be attached to the clothing-type garments using, for example, magnets, buttons, and other fasteners.

The front shell 12 may be exchangeable such that, the front shell 12 can have various patterns, sizes, colors, shapes, animal faces, etc. The front shell 12 may accessorize the outside of the face mask 10. The face mask 10 may include a head strap 28 attached to the front shell 12 for holding the face mask 10 to a user's head.

The front shell 12 has inlet holes 18 for allowing incoming air to pass in to the face mask 10 and through to the filter 14, where the filter 14 filters particulate elements from the air. The filter 14 is secured between the front shell 12 and the support 16.

The filter 14 may be made of a biodegradable material such as sucrose or a nano material. The biodegradable material may be soluble such that, when disposed of, the filter 14 does not contribute further pollution (e.g., in a landfill).

The front shell 12 also has exhale ports 20 separate from the inlet holes 18, which allow exhaled air to pass out of face mask 10. The exhale ports 20 allow exhaled air to outlet the face mask 10 so that the exhaled air does not have to pass back through the inlet holes 18 thereby degrading the filter 14 from the inside. The exhale ports 20 exit downward and away from the mouth and nose of the user. This may advantageously direct exhaled air away from the face mask 10 and reduce fogging where the user is also wearing eyeglasses.

The exhale ports 20 are in fluid communication with outlet valves 22 on the support 16. The outlet valves 22 are one-way valves and only allow for the exhaling of air from the inside of the face mask 10 and out to the environment. The outlet valves 22 are one-way in that they do not allow air to pass from the outside of the face mask 10 in to the respiratory system of the user.

The face mask 10 includes a face seal 24 attached to the periphery of the support 16 for providing a flexible and air-tight seal around the nose and mouth of the user. The face seal 24 provides a snug seal to the user's face and does not allow air to pass in through anything but the filter 14. The face seal 24 is located behind the front shell 12 and contacts the users face to make an air tight seal against the skin. This forces all of the air intake through the front shell 12 and through the filter 14.

In some embodiments, the face seal 24 is made of silicone. The face seal 24 may also include a phase change material such as a cooling gel to cool the user's face in warm environments or to warm the user's face in cool environments. In some cases, the face seal 24 is customized for a specific user, in other cases the face seal 24 can flexibly accommodate a variety of shapes and sizes of a user's face. The face seal 24 may also be flexible such that a user can move their mouth and face (for example, to talk) while continuing to maintain an airtight seal with the user's face. In some cases the face seal 24 is not completely air tight, however, the more air that passes between the face of the user and the face seal 24, the more opportunity the face seal 24 will not filter pollutants through the filter 14.

The front shell 12 includes a pair of shell attachment members 32 located at the sides of the front shell 12. The front shell 12 includes a top shell connector 33 located at a nose position on the inside of the front shell 12 for attaching to the support 16. The support 16 has corresponding inner attachment members 30 for hingedly attaching to the shell attachment member 32 and an upper attachment 37 for removably attaching to attach to the top shell connector 33.

The inner attachment member 30 and shell attachment members 32 may be, for example, clips or other mechanical devices that removably attach the front shell 12 to the support 16.

Figure 6B:
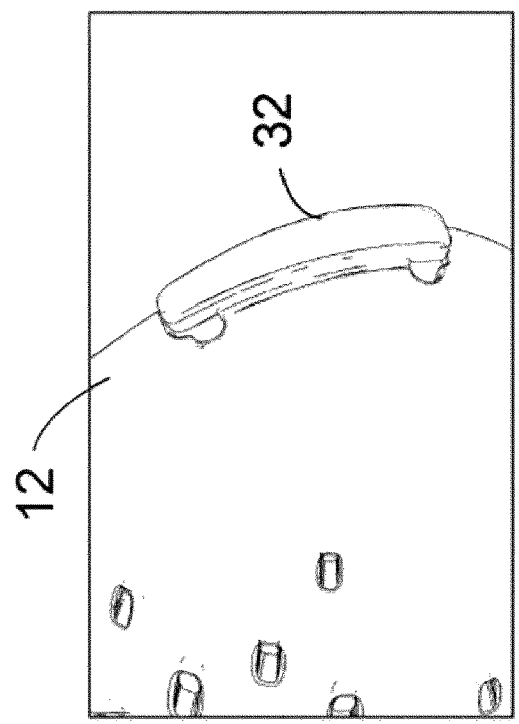
FIGS. 6A and 6B are an inside view and a detailed view of a front shell of the face mask of FIG. 1.
Figure 6A:
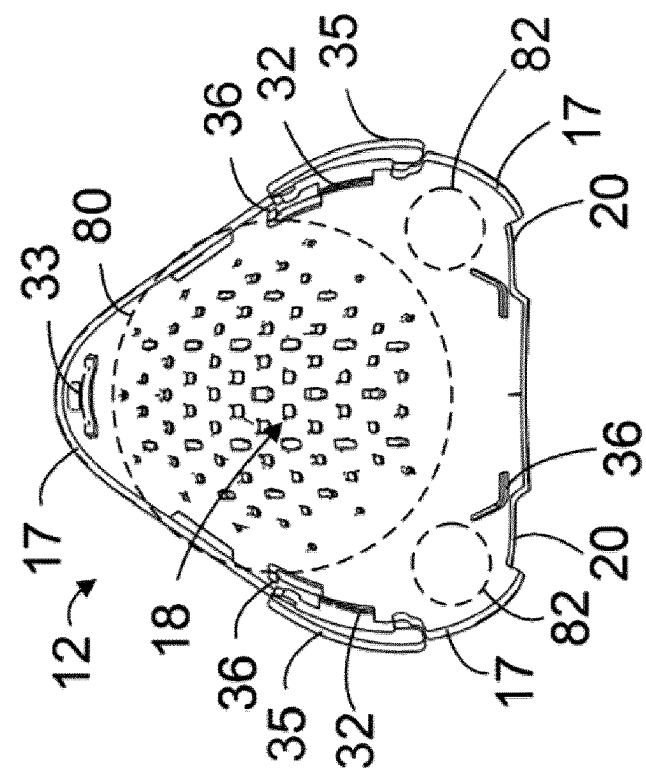

Referring now to FIGS. 6A and 6B, illustrated therein is an inside view of the front shell 12. The front shell 12 may be removable, by a user, from the support 16 to facilitate exchange of the filter 14. The front shell 12 and support 16 are hingedly coupled at the top shell connector 33 (of the front shell 12) and the upper attachment 37 (of the support 16) and snap together at the side of the face mask 10 to the shell attachment members 32 (of the front shell 12) and the inner attachment members 30 (of the support 16). The front shell 12 includes an external release member 35 on the shell attachment member 32.

The external release member 35 may have pressure applied by the user in an outward direction to disengage the shell attachment member 32 from the inner attachment member 30 and thereby opening the face mask 10 like a clam shell. The user then pivots the front shell 12 upwards about the upper attachment 37 and top shell connector 33. The upper attachment 37 and the top shell connector 33 may further removably disengage, such that the front shell 12 can be fully removed from the support 16. The external release member 35 acts as finger pick. The user's finger can slot under the face seal 24 and the external release member and open the front shell 12.

The front shell 12 also has filter registration members 36. The filter registration members 36 are located inside the front shell 12 to align the filter 14 when connecting to the support 16. The front shell 12 includes at least four of the filter registration members 36. The front shell 12 may include a smooth to rough surface texture to further distinguish filter alignment area.

The front shell 12 has the inlet holes 18 that are formed in a pattern 80 in the central area of the face mask 10. The front shell 12 also has outlet areas 82 without holes that align with the outlet valve 22. The filter 14 is configured and sized to cover the pattern 80 of inlet holes.

Figure 7A:
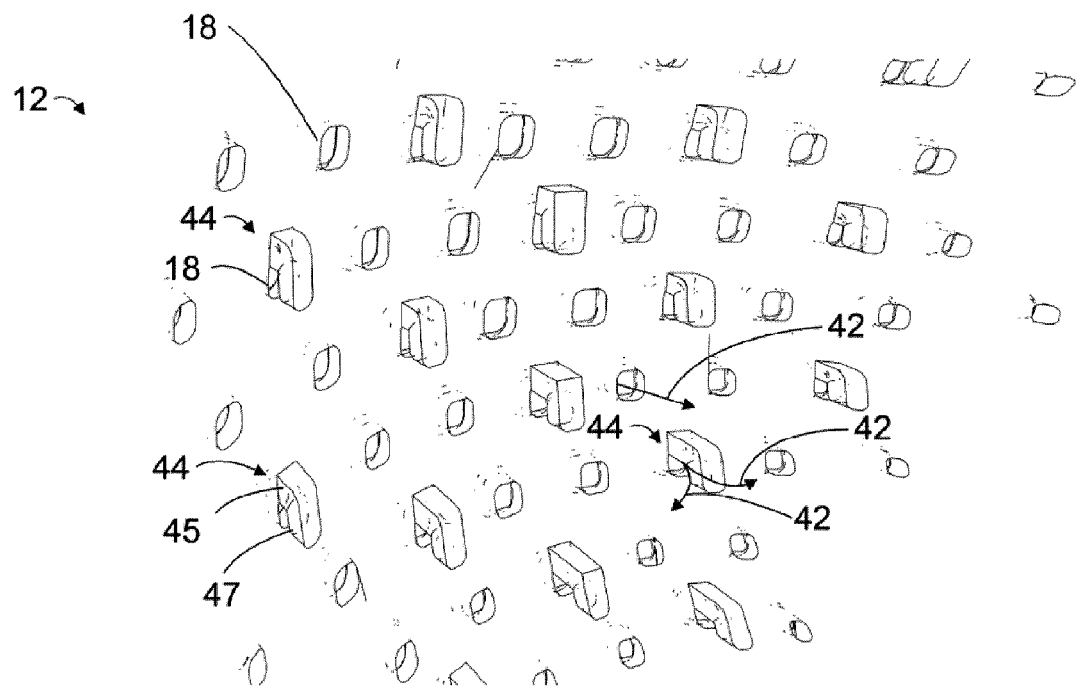
FIGS. 7A and 7B are close up perspective and side views of the front shell of FIG. 6.
Figure 7B:
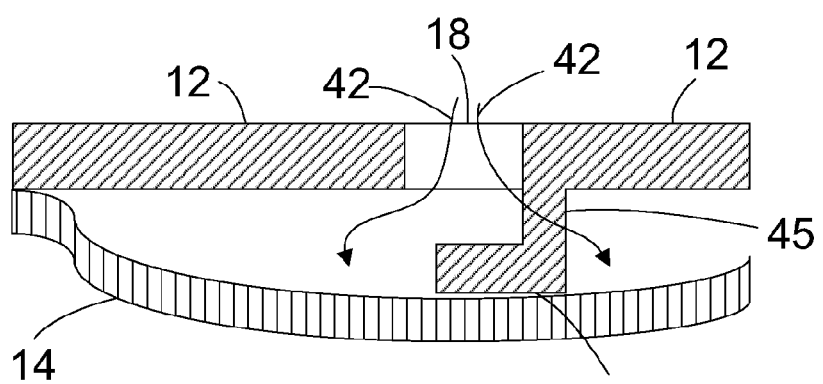

Turning now to FIGS. 7A and 7B, illustrated therein are the inlet holes 18, in accordance with an embodiment. At least one of the inlet holes 18 have airflow stand-offs 44 extending from an inside surface of the front shell 12 and adjacent the inlet holes 18 for preventing the filter 14 from being positioned directly on the inner surface of the front shell 12. The airflow stand-offs 44 may provide improved airflow as inward airflow 42 will also pass through the filter 14 at locations not directly in front of the inlet holes 18.

Each airflow stand-off 44 may have a protrusion section 45 and an overhang section 47. The protrusion section 45 projects outward from the inner face of the front shell 12. In some cases, the protrusion section 45 protrudes from the surface of the front shell 12 at about a distance equal to the size as the adjacent inlet hole 18. The overhang section 47 projects from the protrusion section 45 (for example at a right angle) to cover at least some of the adjacent inlet hole 18. In some cases, the overhang section 47 is about the same size as the adjacent inlet hole 18. The overhang section 47 may inhibit the airflow stand-off 44 from puncturing the filter 14, which could otherwise render the filter 14 ineffective and remove the advantage of pushing the filter 14 off of the surface of the front shell 12 to increase the surface area that is used for airflow.

The airflow stand-offs 44 may provide airflow 42 around the overhang section 47 thus increasing the area of airflow over the face of the filter 14. In an embodiment, each airflow stand-off 44 is not directly adjacent to another airflow stand-off 44. In an embodiment, the airflow stand-off 44 is surrounded by inlet holes 18 without airflow stand-offs 44. In a further embodiment, about one of every three inlet holes 18 has an adjacent airflow-stand offs 44. The airflow stand-off 44 improves airflow and increases the surfaces area to the filter 14. The airflow stand-off 44 can also be used to create visible effect.

Figure 8:
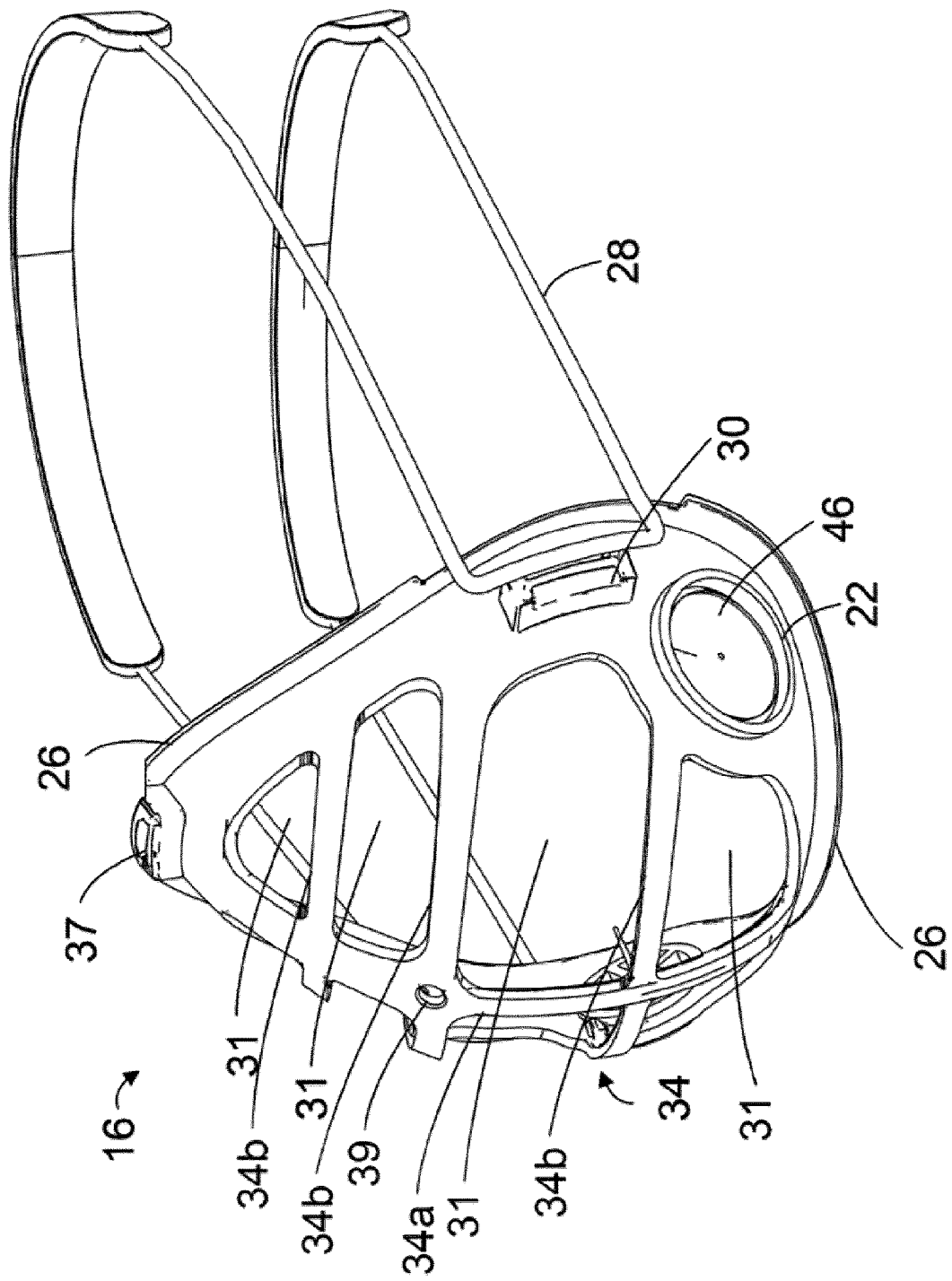
FIG. 8 is a perspective view of a support and a head strap of the face mask of FIG. 1.
Figure 9:
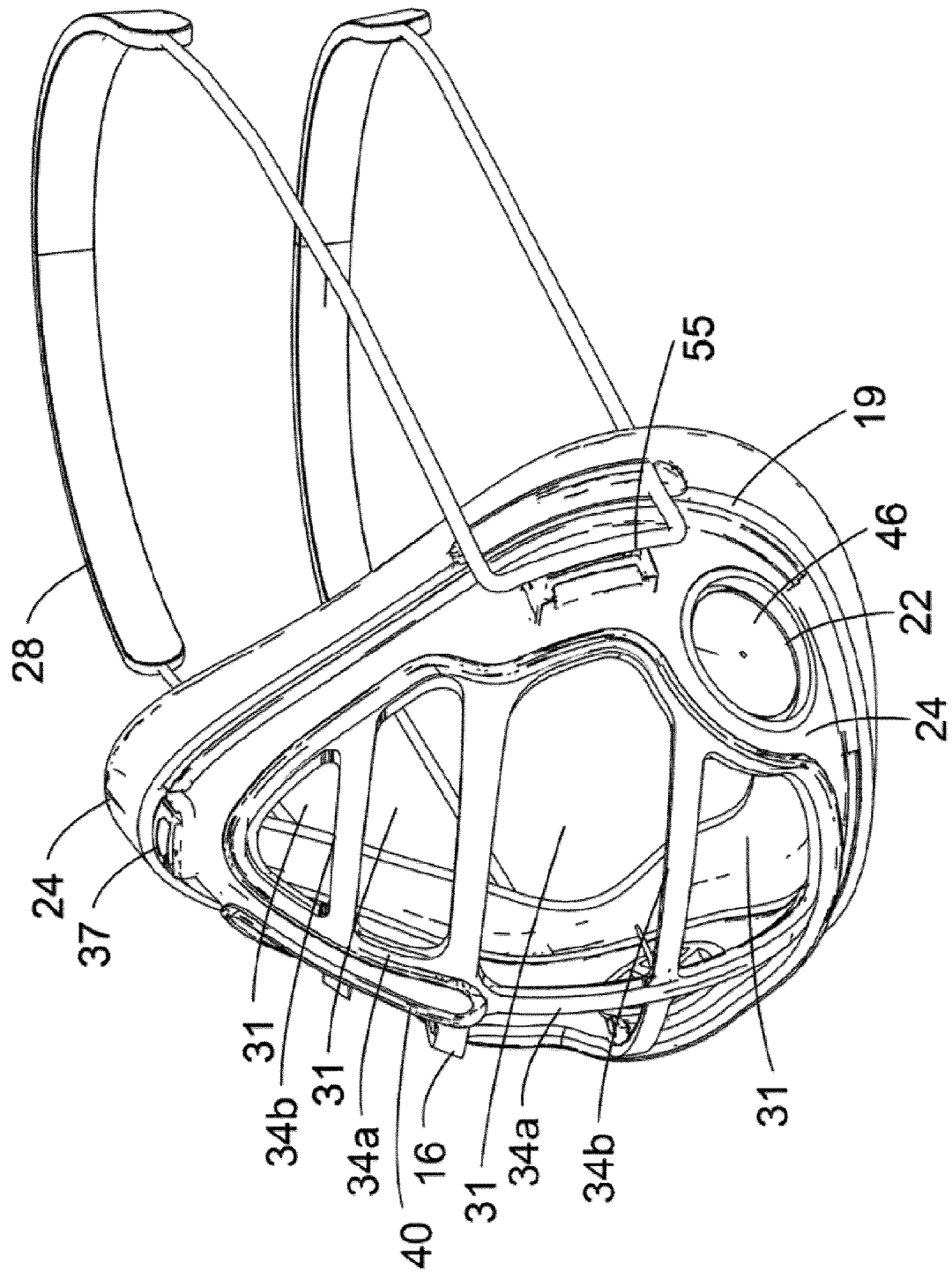
FIG. 9 is a perspective view of the support with an over molded face seal and a head strap of the face mask of FIG. 1.

Turning now to FIGS. 8 and 9, illustrated therein is the support 16 and the face seal 24. The support 16 includes a framework 34 having longitudinal 34a and transverse frame members 34a, 34b to support the filter 14 and open area 31 for allowing air to flow through. In an embodiment, the framework 34 includes a central longitudinal frame member 34a and at least two transverse frame members 34b. The framework 34 may include an antimicrobial polymer and plastic. The filter 14 rests between the front shell 12 and the framework 34 and over the open area 31. The framework 34 may support attachment to the head strap 28. The framework 34 may also be adhered to another material and may have mounting features to be attached in some other way (stitching, clips, etc.) to other surfaces and materials.

The support 16 includes a connection rim 26 for attaching to the face seal 24. The face seal 24 can be attached (e.g., glued) to the support 16. Alternatively, the face seal 24 may be over moulded to the support 16.

In addition to sealing on the user's face, the face seal 24 seals the perimeter of the filter 14 between the support 16 and the front shell 12. The face seal 24 acts as a gasket surrounding the outside edges of the open area 31 to mate with the perimeter of the filter 14. The face seal 24 seals the perimeter of the filter 14 by creating a compression pinch when the front shell 12 is attached to support 16. This forces all inhalation through the filter 14 without any air travelling around the filter 14 and then through the open area 31. The resistance of the air flow through the valves 20 is weaker than through the filter 14 on exhale and on inhale the valves 20 seal making the only ingress through the filter 14.

The face seal 24 includes a nose seal 40 extending down along the central longitudinal frame member 34a. The nose seal 40 may include a connector post 25 (seen at FIG. 5) which connects to a post hole 39 in the central longitudinal frame member 34a. The nose seal 40 is positioned to seal a pair of nose portions 38 of the filter 14 to provide an airtight seal between the filter 14 and the support 16.

The face seal 24 has a mating surface 19 that seals against a peripheral surface 17 of the front shell 12. The face seal 24 has attachment apertures 21 for providing access and sealing around the inner attachment members 30. Similarly, the face seal 24 also has a top aperture 23 for providing access and sealing around the upper attachment 37.

Figure 4:
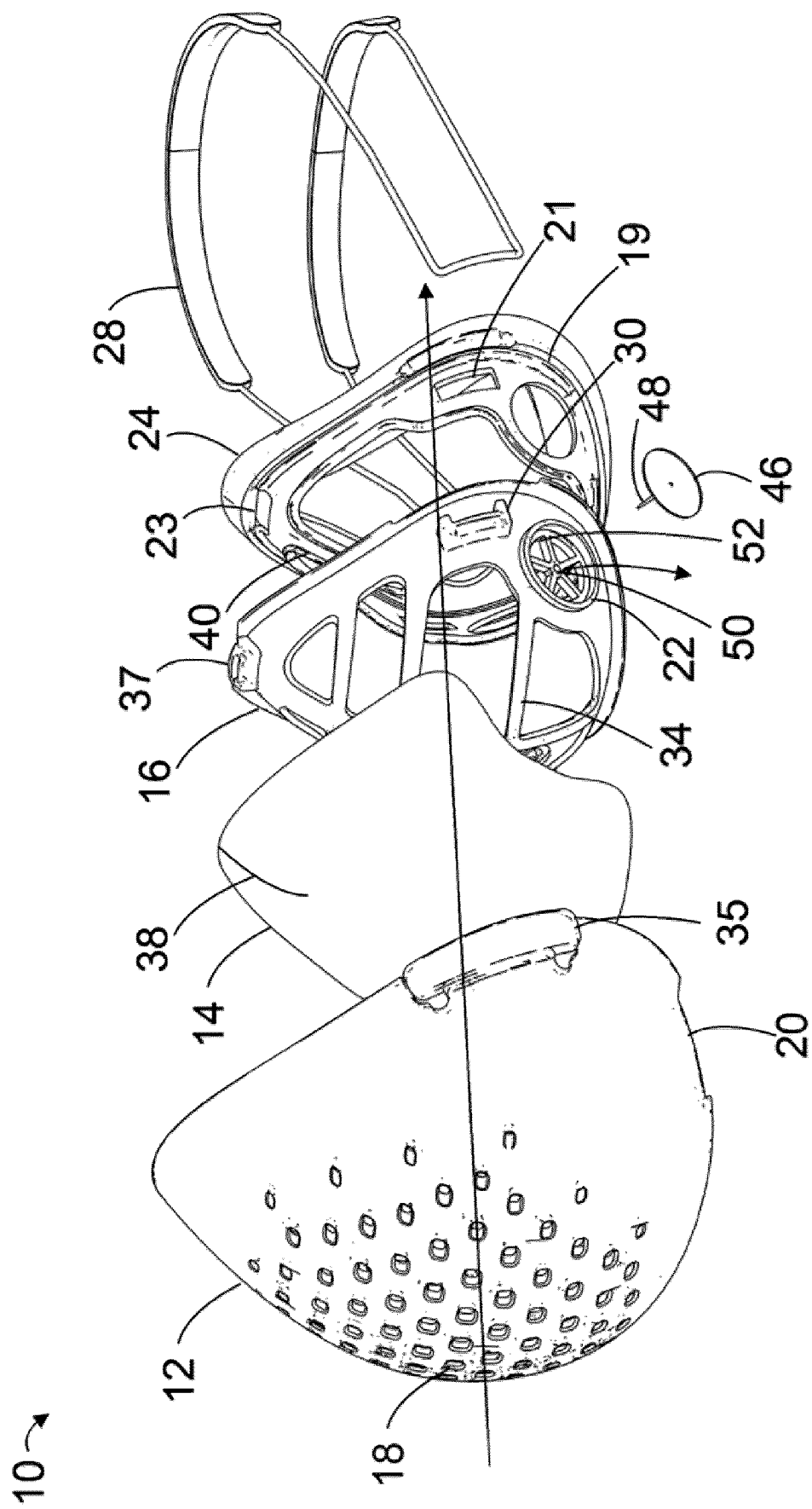
FIG. 4 is an exploded perspective view of the face mask of FIG. 1.
Figure 5:
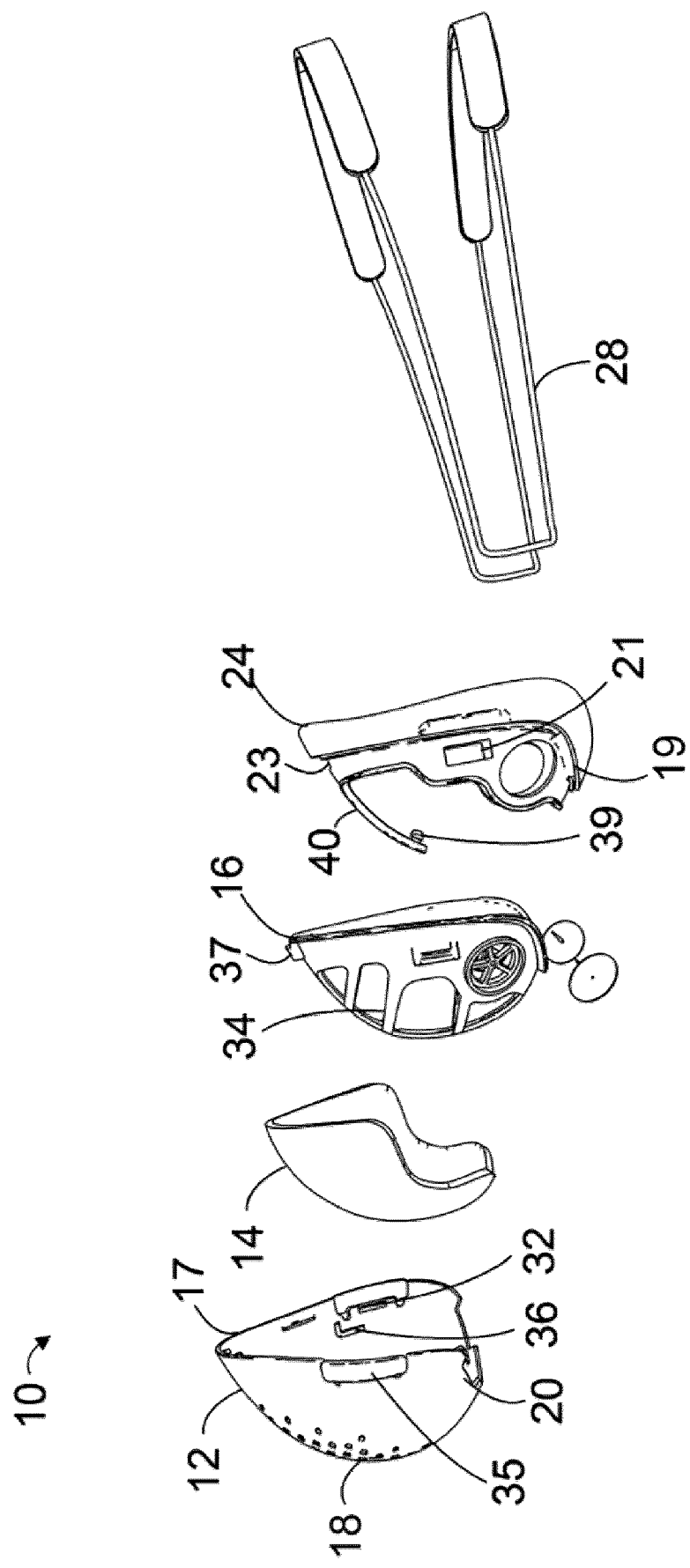
FIG. 5 is an exploded side view of the face mask of FIG. 1.

As seen in more detail at FIG. 4, the support 16 has exit valves 46 that lead to the exhale ports 20 on the front shell 12. The exit valve 46 is a one-way valve that has a post 48 that passes through a hole 50 on the support 16. The exit valve 46 rests on a seat 52 of the support 16 to prevent air from passing inward. The exit valve 46 may be made of silicone or another flexible material, as is known in the art.

In some embodiments, the support 16 includes a humidity and odor absorbing capsule. The humidity and odor absorbing capsule may be located along the inside surface of support 16. The humidity and odor absorbing capsule may reduce any excess moisture and unpleasant odors to give the user a more pleasant and comfortable experience.

Figure 10:
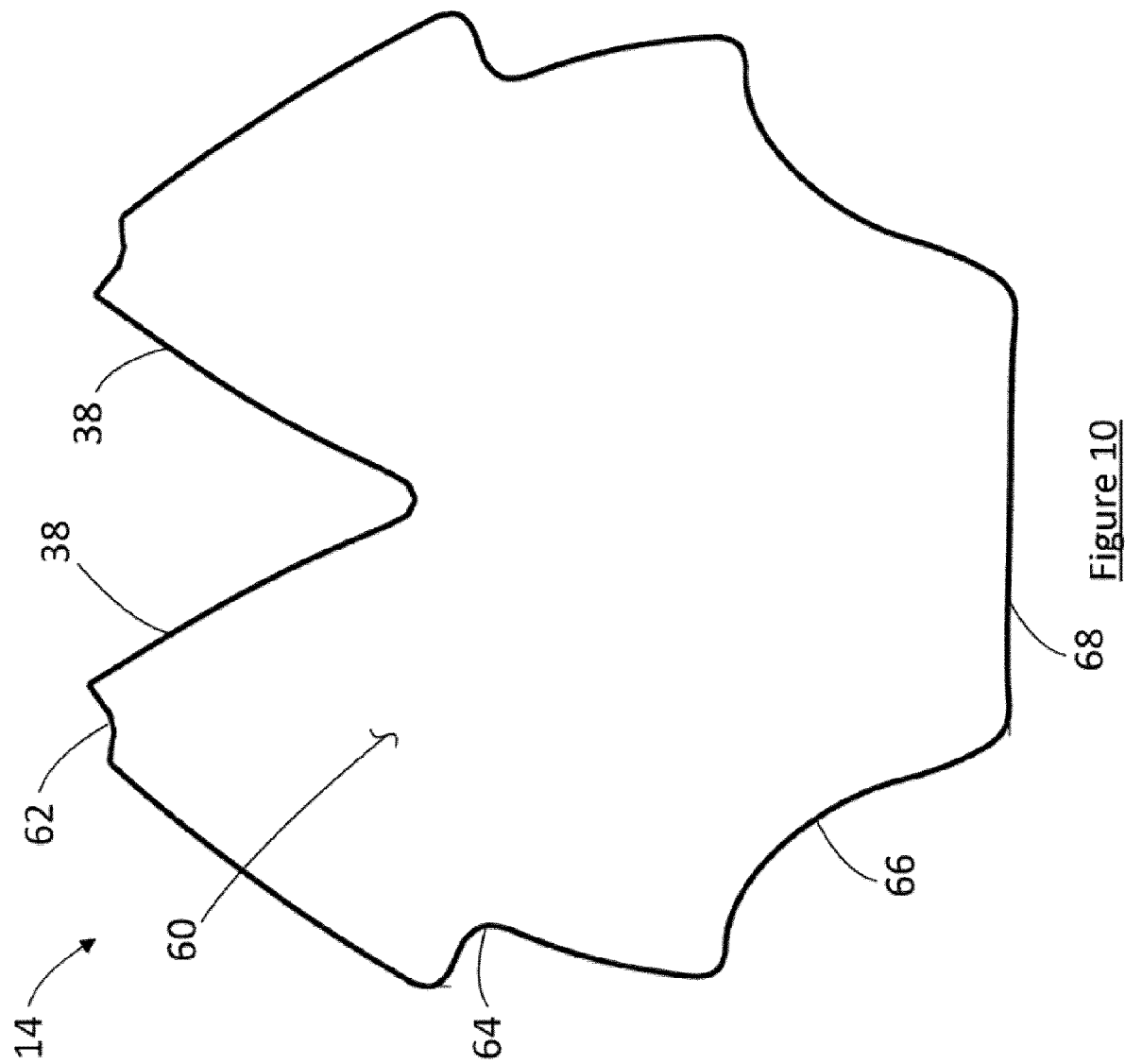
FIG. 10 is a front view of a filter, in a flat orientation, of the face mask of FIG. 1.

FIG. 10 illustrates a flat layout of the filter 14. The filter 14 may be a replaceable melt blown, technostatic, carbon, nano, or biodegradable nano filter. When in position, the filter 14 is housed between the front shell 12 and support 16. The filter 14 filters pollutants from the air before the air reaches the user. The filter 14 is flat when not assembled and curves to become a three dimensional form when placed in the face mask 10. The filter 14 may be generally symmetrical about a center axis. When the filter 14 is folded together for use, the nose portions 38, separated by a central nose slit, mate together to form the three dimensional form for insertion into the face mask 10. The nose portions 38 align with the nose seal 40 of the face seal 24 on the framework 34 of the support 16. The perimeter of the filter 14 seals with the face seal 24.

The filter 14 includes a filter surface 60 that interacts with the surface of the front shell 12. The filter includes top cut outs 62, side cut outs 64, bottom cutouts 66, and bottom edge 68 that match with the filter registration members 36 on the inner surface of the front shell 12. When the cut outs 62, 64, 66, on the flat filter 14 are placed between the front shell 12 and the support 15, the filter 14 goes from two dimensions to three dimensions. The filter 14 is pinched at the periphery to causes an airtight seal. The cut outs 62, 64, 66 allow the filter 14 to fold to the desired shape in order to be pinched and prevent air passage around the filter 14.

Figure 11:
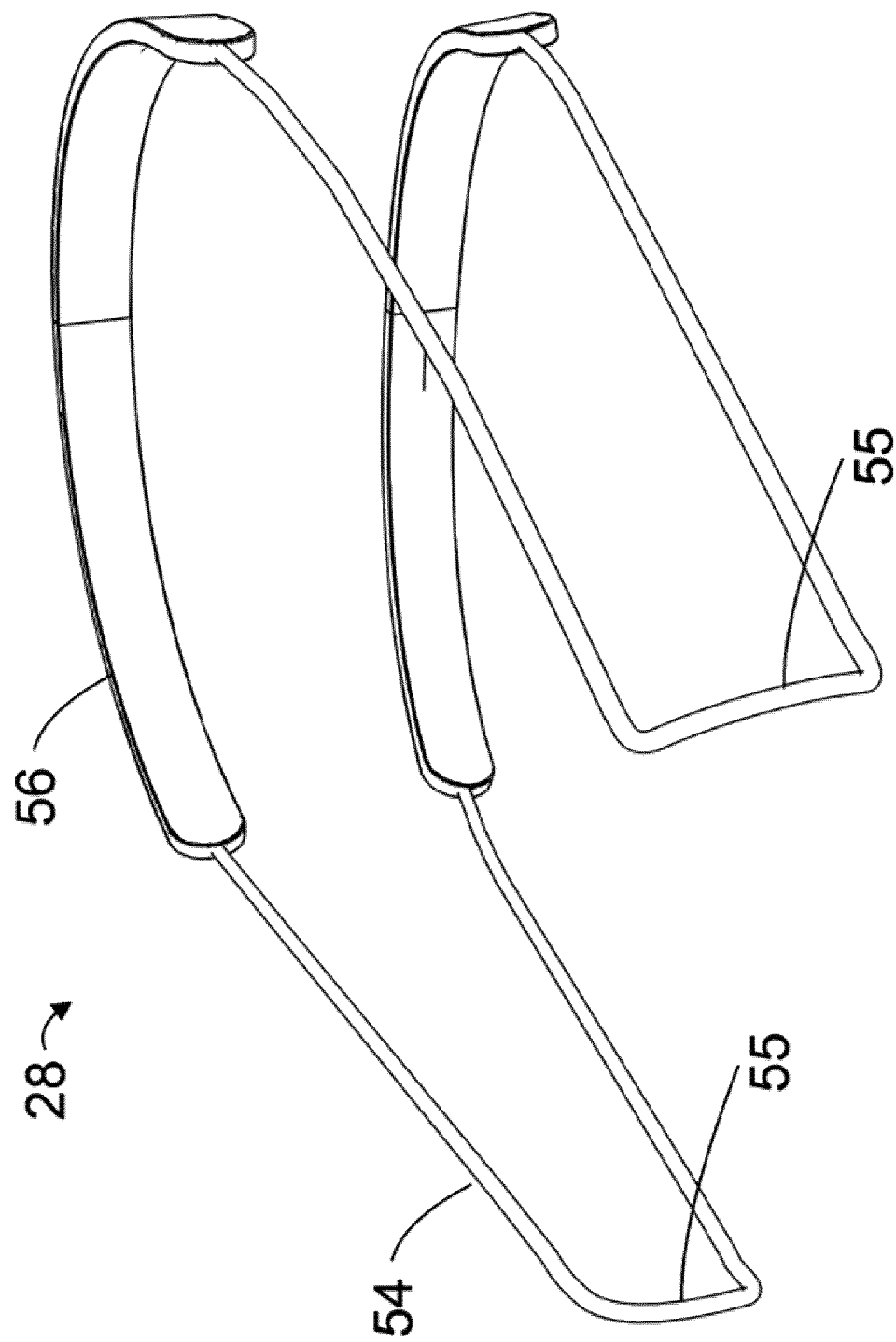
FIG. 11 is a perspective view of the head strap of the face mask of FIG. 1.

FIG. 11 shows a front side perspective of the head strap 28 of the current invention. The head strap 28 has an elastic component 54 and an inelastic component 56. The head strap 28 can be made of materials such as silicon, plastic, polyurethane and leather. The head strap 28 may be elastic in nature to allow a comfortable compression of the face seal 24 on the user's face. The head strap 28 may feature a branded top head band. The head strap 28 may also include silicon or plastic straps having a strap attachment point, adjustable holes settings and band elasticity. The head strap 28 has a mask attachment 55 for connecting to the face mask 10 at the inner attachment members 30.

Figure 12:
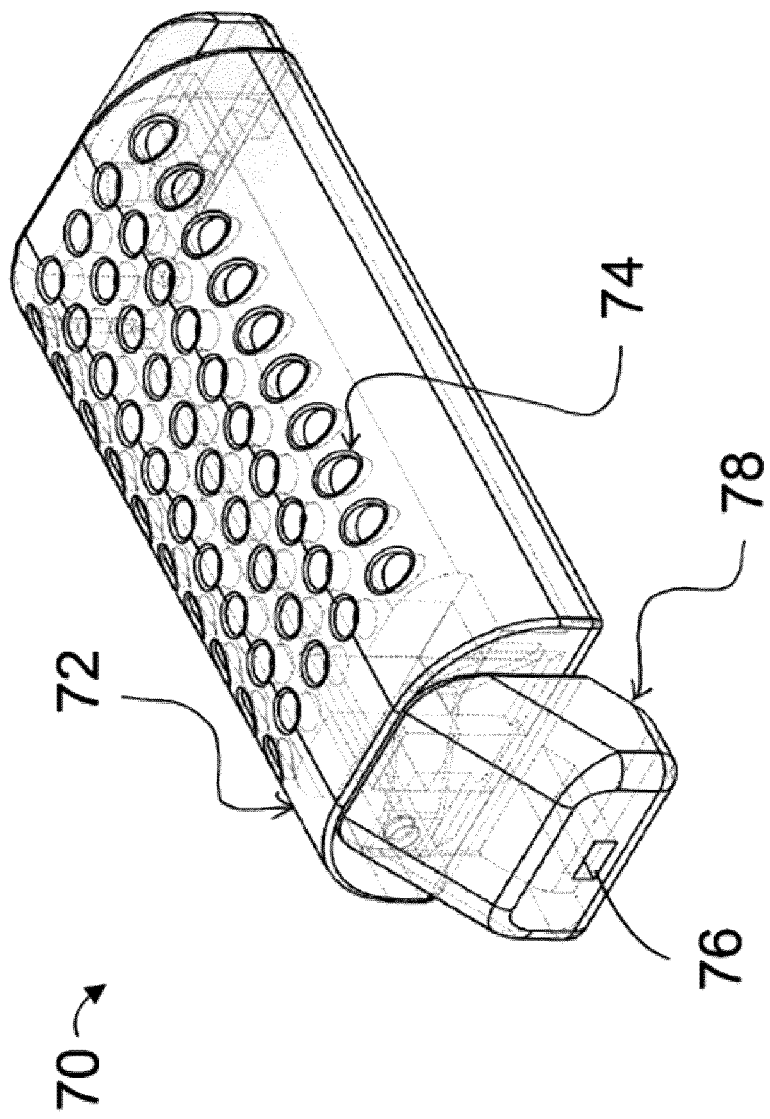
FIG. 12 is a perspective view of a pollution sensor for a face mask, in accordance with an embodiment.

FIG. 12 shows a top side view of a pollution sensor 70 to be mounted to the head strap 28 of the face mask 10. The pollution sensor 70 monitors the amount of particulate in the air. The pollution sensor 70 includes a housing 72 having vent holes 74 to allow for air flow around inner components of the pollution sensor 70. The housing 72 may be molded together during manufacturing and any battery may not be replaceable.

The housing 72 includes band attachments 76 for attaching the housing 72 to the head strap 28. The pollution sensor 70 includes an electronic circuit (e.g., pollution circuit 122 described with reference to FIG. 15) that reads the amount of pollutants in the air. The electronic circuit includes a communication system for communicating the reading data between the pollution sensor 70 and an application on a user communication device.

The pollution sensor 70 includes a tension switch 78 having a spring that turns the pollution sensor 70 on when the user puts on the face mask 10 by pulling on the head straps 28 and putting tension on the tension switch 78. The tension switch 78 turns off when the user removes the face mask 10, taking the tension off of the tension switch 78. The tension switch 78 may allow for improved tracking of pollution data as the pollution sensor 70 will only record pollution data when the user is wearing the face mask 10 described in more detail with reference to FIG. 15.

FIGS. 13A and 13B illustrate a pollution sensor 170 for mounting to a head strap 171 of a face mask (e.g., face mask 10), in accordance with a further embodiment. The pollution sensor 170 includes a housing 172 (e.g., housing 72) and a tension switch 178 (e.g., tension switch 78).

As seen from FIG. 13A, the pollution sensor 170 may also include an electronic circuit 180 (e.g., pollution circuit 122), a battery 182 for supplying power to the electronic circuit 180, and transceiver 184 (e.g., Bluetooth™) for sending and receiving signals.

As seen in FIG. 13B, the head strap 171 has an elastic component 154 and an inelastic component 156. The tension switch 178 and transceiver 184 are fixed between the elastic component 154 and the inelastic component 156. The electronic circuit 180 may also include vent holes 174 for allowing airflow into pollution sensors. The electronic circuit 180 is able to communicate with the tension switch 178 and transceiver 184.

The electronic circuit 180 includes a clip 186 that is removably attachable to the inelastic component 156 of the head strap 171. The electronic circuit 180 may be removable to provide the desired level of functionality desired by the user. For example, where the user desires to only monitor whether the face mask is on and not take any pollution readings, the electronic circuit 180 may be removed and turned off. If pollution sensing capability is desired, the user may attach the electronic circuit 180 to the head strap 171.

Further, the electronic circuit 180 may be clipped somewhere else on or near the user (e.g., on another article of clothing) and take pollution reading from there, as desired by the user to improve pollution reading and/or user comfort.

FIG. 13C illustrates a tension switch 178 (e.g., tension switch 78) in an open position and a tension switch 179 in a closed position, in accordance with an embodiment. Within the housing 172 of the tension switch 178, the head strap 171 is attached to a leaf spring 188. The leaf spring 188 is made of an electrically conductive material such as metal. The tension switch 178, 179 includes electrical contacts 190 and posts 192 that are fixed to the housing 172 for contacting the leaf spring 188. When the head strap 171 is not pulled, the tension switch 178 is open, the leaf spring 188 is out of contact with the electrical contacts 190 and rests on the posts 192. When the head strap 171 is pulled away from the housing 172, the leaf spring 188 moves into contact with the electrical contacts 190, completing the electrical circuit, and the tension switch 179 is closed. The tension switch 178, 179, may include a stop to prevent the head strap 171 from pulling completely out of the housing 172.

Figures 14A, 14B, 14C:
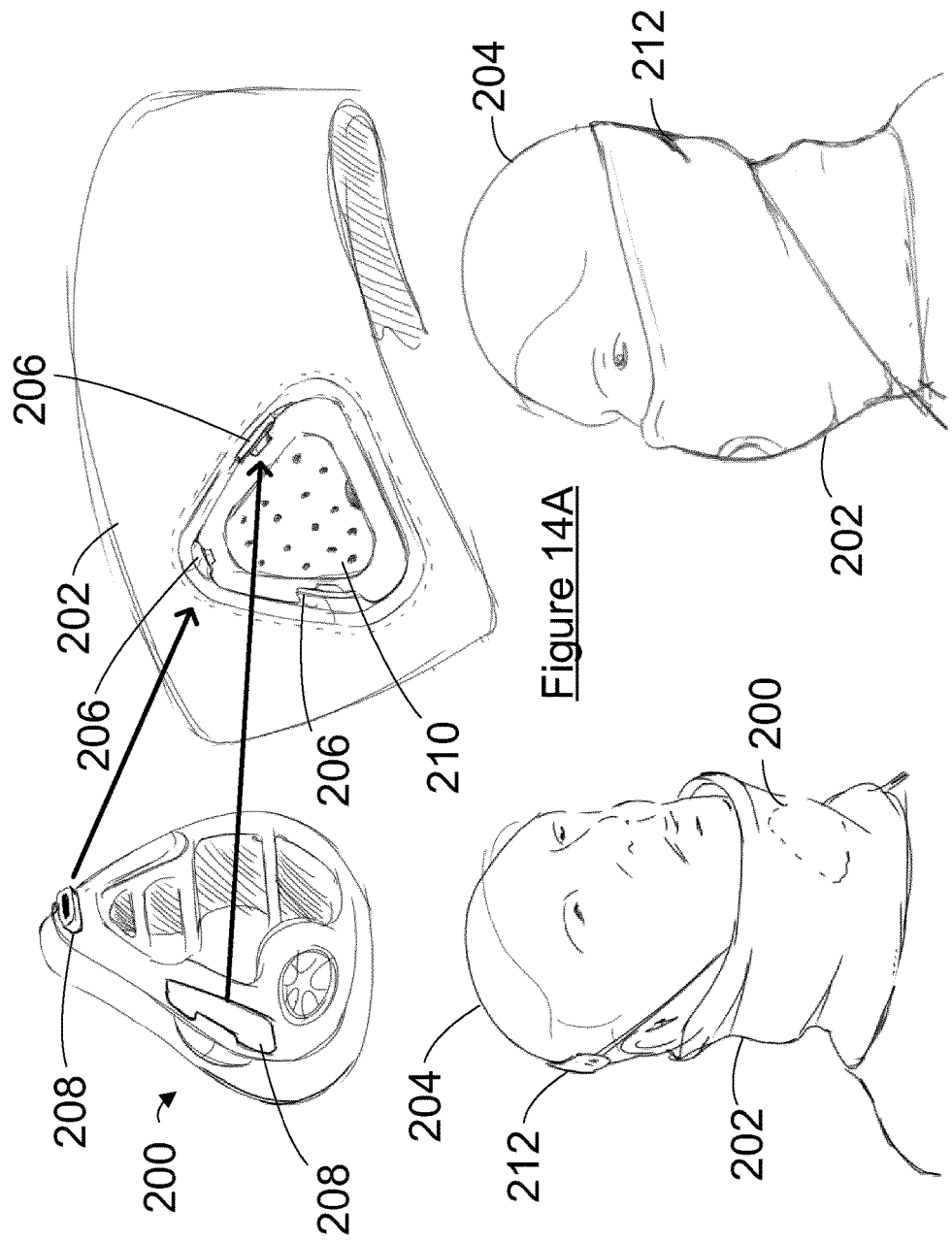
FIGS. 14A, 14B, and 14C are exploded and perspective views of a face mask in a scarf, in accordance with a further embodiment.

Turning now to FIG. 14A-14C, illustrated therein is a face mask 200 embedded in a scarf 202, in accordance with an embodiment. The scarf 202 includes attachment cups 206 that are stitched or welded into the scarf material. The attachment cups 206 function similar to the front shell 12 (as described with reference to FIGS. 1-11) to attach to snap features 208 (e.g., 30, 37) on the face mask 200. The attachment cups 206 seal a filter 210 between the face mask 200.

The face mask 200 can be worn by the user 204, when not in use (FIG. 14B). When in use (FIG. 14C), the scarf 202 covers a head strap 212.

Figure 15:
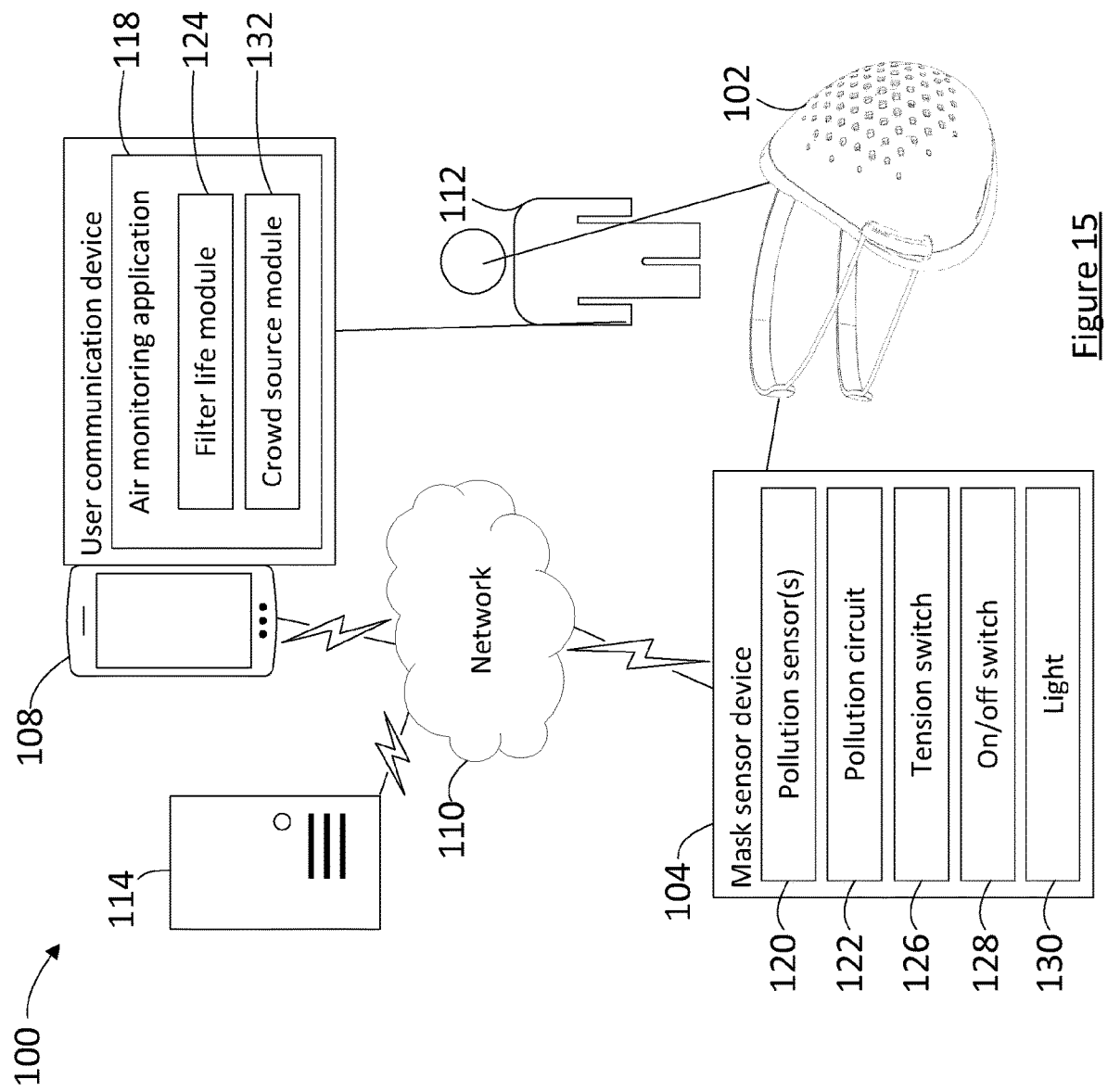
FIG. 15 is a block diagram of an air monitoring system, in accordance with an embodiment.

Turning now to FIG. 15, illustrated therein is an air monitoring system 100, in accordance with an embodiment. The air monitoring system 100 includes a face mask 102 for filtering air, such as the mask described with reference to FIGS. 1 to 11. The face mask 102 may include a mask sensor device 104 (such as the pollution sensor 70, 170 described with respect to FIGS. 12, 13A, 13B, 13C) having a pollution circuit 106. The mask sensor device 104 is mounted externally to the face mask 102 so that the user's exhaled breath (including humidity, carbon dioxide, and other gasses) does not skew readings of the mask sensor device 104.

The air monitoring system 100 includes a user communication device 108 (such as a mobile device, personal computer, smartphone, or the like) in communication with the mask sensor device 104 for receiving Air Quality Readings (AQRs) from the mask sensor device 104. The mask sensor device 104 communicates directly with the user communication device 108 (e.g. via Bluetooth™) or indirectly with the user communication device 108 via a network 110 (such as a mobile network and/or the Internet). The user communication device 108 may be used by a user 112 wearing or using the face mask 102. The mask sensor device 104 and the user communication device 108 may also communicate with a server 114 via the network 110.

The mask sensor device 104 can be located on the strap of the face mask 102, inside the face mask 102, on user communication device 108, and/or on a case of the user communication device 108. In further embodiments, the mask sensor device 104 may be provided in another location on the user 112, such as in a wristband, clothing, a smart badge on a lanyard, or integrated into the user communication device 108.

In some cases, the pollution sensor 70 is not in the face mask 10 as human breath may include humidity and carbon dioxide and may skew the readings of the sensors.

The user communication device 108 includes an air monitoring application 118 that is purpose built for interaction with the user 112. The air monitoring application 118 may display, on the user communication device 108, air quality ratings from the sensor to help the user 112 make decisions on whether to wear the face mask 102 or not. The user communication device 108 may display the AQRs as pollution data in user friendly graphical displays.

The air monitoring application 118 and the mask sensor device 104 work independently however, the air monitoring system 100 can be particularly advantageous when working together. The mask sensor device 104 samples the local air and measures the local air quality at varied time and geographic intervals to generate the AQRs, as seen from FIGS. 16A-C. The AQRs are collected from the mask sensor device 104 and sent to the user communication device 108 which may also be uploaded to the server 114.

The mask sensor device 104 includes at least one air pollution sensor 120 for measuring air quality readings (AQRs) in the environment that the user 112 breathes and inhales. The air pollution sensors 120 may include any one or more of a humidity sensor, a temperature sensor, a dust sensor (e.g. light-based), a variety of sensors for measuring CO, NO2, O3, SO2, PM2.5, PM10, and other atmospheric sensors for monitoring air quality or allergen. Accordingly, the AQRs may include readings for any one or more of humidity, temperature, dust, CO, NO2, O3, SO2, PM2.5, PM10, and other air quality or allergen information.

In a particular embodiment, the air pollution sensor 120 focuses an infrared light emitting diode (LED) through a lens to focus the light on a photodiode. Air passes in through the vent holes (74) and when particles cross the beam of light a disturbance is created in the light rays, which then changes the pick up on the photodiode and changes the voltage that the photodiode is receiving or returning. The signal from the air pollution sensor 120 is converted into a digital signal.

In certain embodiments, the face mask 102 includes a pollution sensor placed behind the filter. The AQRs from this pollution sensor may also provide an up-to-date and accurate reading of how much pollution is making it through the filter.

The mask sensor device 104 also has a pollution circuit 122 for performing certain operations of the mask sensor device 104. The pollution circuit 122 includes a memory having a local mask database for storing the AQRs. The pollution circuit 122 also includes a processor for processing the AQRs, creating a personal air quality index, a transceiver for sending and receiving the AQRs, and a power supply (such as a rechargeable or replaceable battery) for supplying power to the pollution circuit 122.

The server 114 receives AQRs from at least one mask sensor device 104 and location data from the air monitoring application 118 to create a three dimensional, real-time map of the AQR's. The user communication device 108 measures location data from, for example, an onboard GPS (global positioning system) and sends the location data to the server 114. The location data and collected AQRs may be customized to be in the form of the respective Air Quality Index (AQI) for that country or location. AQI, may be, for example, a number on a scale of 0-500, where low values are good and progress to higher values that indicate hazardous pollution.

From the specific time and location of the AQRs, the server 114 determines an AQR accuracy value which may degrade over time and distance. The air monitoring application 118 measures the proximity of the user communication device 108 to existing AQRs and calculates, based on distance, time, and predictability, an personal AQI and an AQR accuracy for the user. If the AQR accuracy is above a predetermined threshold (an accepted confidence level) the personal AQI and AQR accuracy is reported to the user via a display on the user communication device 108. If the AQR accuracy is below the predetermined threshold, and the mask sensor device 104 is enabled and is currently being worn, than the air monitoring application 118 will send a prompt to the mask sensor device 104 to sample the air. The mask sensor device 104 will perform a new pollution measurement and a new AQR will be stored and sent to the server 114. The server 114 will update the AQR map.

The server 114 also determines future or current air quality without a current AQR from the AQR data to create AQR predictions. The server 114 uses pollutant levels and patterns, based upon prediction factors including but not limited to time of day, air current, temperature, humidity, and geographic events to determine the AQR predictions.

In various embodiments, the air monitoring system 100 may include the mask sensor device 104 without the user communication device 108, the user communication device 108 without the mask sensor device 104, or both the mask sensor device 104 and the user communication device 108. The air monitoring application 118 operates in a global mode when not paired with the mask sensor device 104.

The air monitoring application 118 operates in a personal mode when the air monitoring application 118 and the mask sensor device 104 are paired to each other. The personal mode allows top level control to come directly from the air monitoring application 118 (e.g., via Bluetooth). The air monitoring application 118 may control the pollution circuit 122 and the pollution circuit 122 responds by sending back string data.

The mask sensor device 104 operates in a local mode, when the user communication device 108 is not linked to the mask sensor device 104. The air monitoring application 118 operates in a local default mode by default.

The air monitoring application 118 may include a filter life module 124. The filter life module 124 determines any one or more of filter life, filter effectiveness, and lifetime usage from the user's breathing rate or airflow, the duration of time the user has worn the face mask 102, and the levels of air pollutants during that time at the user's location from the AQR data. Each filter (for example filter 14) has a set load capacity (e.g. measured in milligrams), that when tested is shown to become saturated and decreases in breathability. The amount of pollutants the user has filtered is determined from the AQRs and the time worn. There is a linear relation between how long the user wears the face mask 102 and the life of the filter.

The filter life module 124 receives time data (e.g., from the tension switch 78, 166) and stores the duration of time that the face mask 102 is on, the user 112 and the users AQR's during that period. An accelerometer in the user communication device 108 monitors activity levels and user entered data about, age, height, and weight, the filter life module 124 determines user breathing rates.

Where the air monitoring system 100 does not include the mask sensor device 104, the filter life module 124 makes default determinations about when the user 112 is using the face mask 102. The default determinations may be adjusted by the user 112.

As the amount pollutants being blocked by the filter adds up, the filter life module 124 will display the life of the filter diminishing. At a certain point as the filter life decreases, the filter life module 124 will prompt the user 112 to replace the filter. The filter life module 124 may also prompt the user 112 to buy more filters and provide a link to an online marketplace where filters can be purchased. In a further embodiment, the filter life module 124 may order and send the filters to the user without intervention from the user 112.

The mask sensor device 104 checks data for relevancy based on context data and relevancy parameters. Based on contextual data from the user communication device 108, the mask sensor device 104 may trigger the air quality measurement. The contextual data may include a change in environment. For example, when the user communication device identifies a change of environment, the at least one pollution sensor is triggered to take and send a new AQR. The contextual data may be based on GPS, WIFI, or other systems present in a conventional user communication device 108. The contextual data may include loss of communication signal, a change in temperature, rapid movement on GPS (e.g., when in a car), and an identification by the GPS when the user is proximal to a busy street.

For example, where the user enters subway, the mobile communication device 108 is out of range of mobile communication, imply that the user is underground, and will trigger the mask sensor device 104 to take a new air quality reading. In another example, where the user and the user communication device 108 goes out of range of WIFI connectivity, and where the user communication device 108 returns to WIFI connectivity, the mask sensor device 104 takes a new air quality reading. In a further example, where the user and user communication device 108 are indoors (e.g., in the office), once the user goes outside and user communication device 108 detects this movement from the onboard GPS and triggers the mask sensor device 104 to take a new air quality reading.

The mask sensor device 104 may include a tension switch 126 (such as the tension switch 78). The mask sensor device 104 may also include an on/off switch 128. When the face mask 102 is not being worn by the user 112, the tension switch 126 is in an off position and the mask sensor device 104 is on an off state. When the face mask 102 is put on, the tension switch 126 changes to on and the pollution circuit 122 goes into a sleep state by default to save battery life. At periodic intervals that are determined by the air monitoring application 118 (where the mask sensor device 104 is connected to the user communication device 108), a signal is sent from the user communication device 108 to wake up the pollution circuit 122 and trigger the air pollution sensors 120 to take samples. Where the air monitoring application 118 is not linked to the mask sensor device 104, the pollution circuit 122 will trigger the air pollution sensors 120 to take readings at predetermined time intervals.

When the pollution circuit 122 is triggered, the air pollution sensor 120 is fired which includes a startup phase, a sampling phase, and shutdown phase. The signal recorded by the air pollution sensor 120 during the sampling phase may be averaged to reduce signal noise. The average signal with the corresponding time and date (including the AQRs) is then recorded as a number and stored in a data string on the internal memory of the pollution circuit 122. The string data is stored in internal memory in case the user communication device 108 and the mask sensor device 104 become temporarily disconnected. When the user communication device 108 and the mask sensor device 104 are connected, the data string is sent from the mask sensor device 104 to the user communication device 108.

In an embodiment, the mask sensor device 104 includes an indicator light 130, for example, an light emitting diode (LED), controlled by the pollution circuit 122.

The pollution circuit 122 flashes the indicator light 130 if pollution levels reach a predetermined threshold (e.g., set by the user 112) for a high level and a low level. The indicator light 130 blinks based on local AQR data if the mask is on the user and the user communication device 108 is not connected to the mask sensor device 104, otherwise the air monitoring application 118 controls the indicator light 130.

For example, if the user 112, via the user communication device 108, creates an alert for 100 on the AQI, then when the air pollution sensor 120 reads a level of 100 or higher (indicating a poor air quality) after sequentially reading a number lower than 100, the indicator light 130 on the mask sensor device 104 will flash red. If the air pollution sensor 120 reads a pollution level to below 100 than the indicator light 130 will flash green at the point when the threshold has been passed. If the pollution levels remain either consistently under or over the threshold, the indicator light 130 will remain off. The indicator light 130 will only flash if the pollution circuit 122 is in an on state. Regardless of whether the pollution circuit 122 is on, the air monitoring application 118 displays a notification to the user 112, where the user threshold is exceeded, based on the global AQI.

In an embodiment, the air monitoring application 118 includes a crowd source sampling module 132. Where there are a plurality of the mask sensor devices 104, at least two mask sensor devices 104 in close proximity may provide AQR data that may be relevant to the other of the two mask sensor devices 104. In this case, it may not be necessary to wake the pollution circuit 122 of a first mask sensor device 104, where a second mask sensor device 104 has previously taken an AQR.

Accordingly, the crowd source sampling module 132 may conserve power on at least one mask sensor device 104. Where there is a high density of mask sensor devices 104, there may be a further reduction in battery usage, and a resulting increase in battery life.

Figures 16A, 16B, 16C:
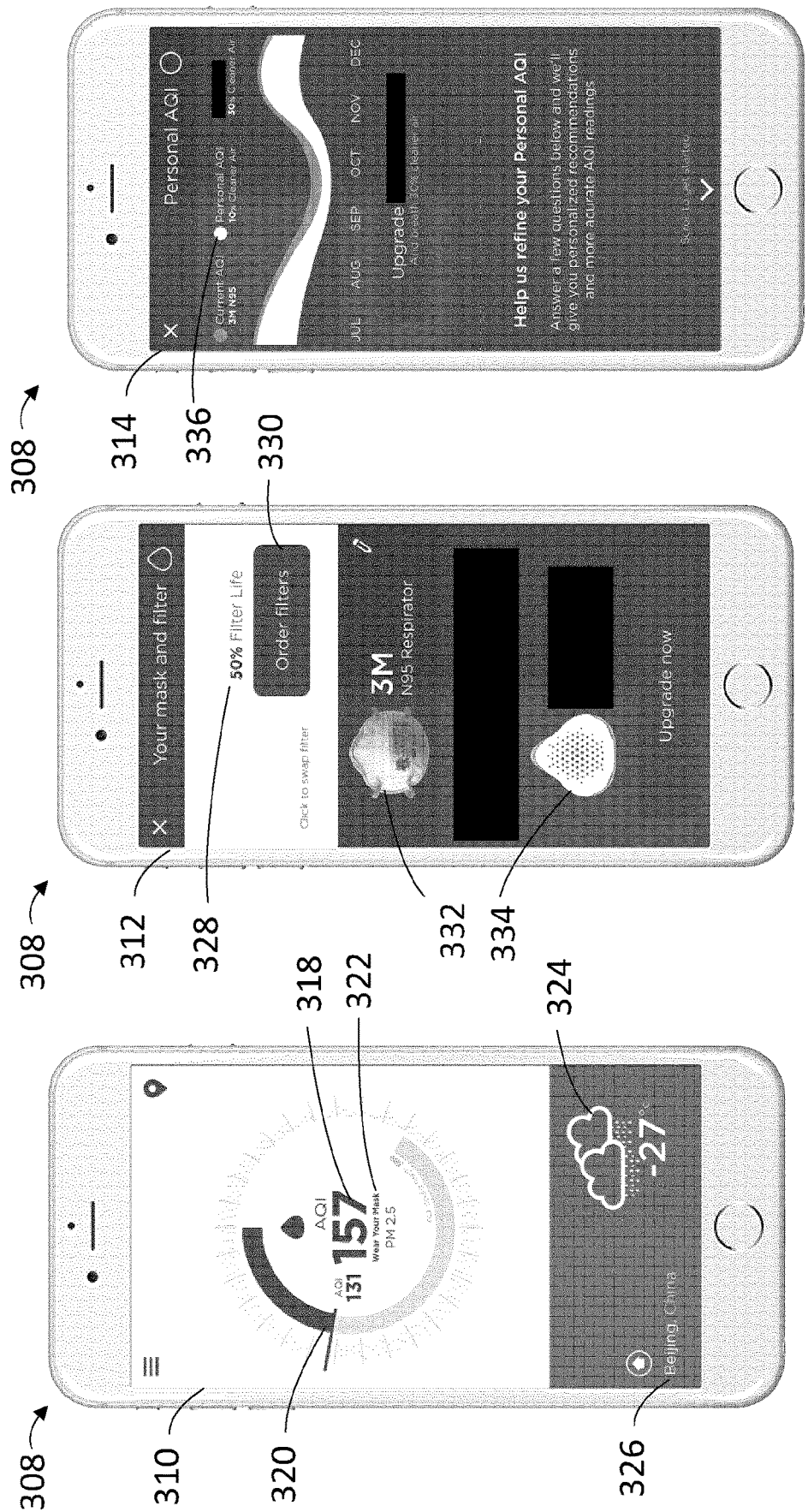
FIGS. 16A, 16B, and 16C are user communication devices of the air monitoring system of FIG. 15.

Turning now to FIGS. 16A-C, illustrated there in is user communication devices 308 displaying various AQR displays 310, 312, 314. The AQR display 310 includes an AQI reading 318 and an AQI gauge 320, showing the AQI on a scale. The AQR display 310 also includes a wear/not wear indicator 322, here recommending that the user wear the face mask. The AQR display 310 also includes a weather indicator 324 showing the local weather forecast for a location 326 (e.g., the user's location). The AQR display 312 includes a filter life indicator 328 showing the percentage of filter life remaining. The AQR display 312 also includes a filter ordering selection 330, which allows the user to exchange an old filter 332 by ordering a new filter 334. The AQR display 314 includes a personal AQI 336 for that user showing historic and current measurements.

While the above description provides examples of one or more apparatus, methods, or systems, it will be appreciated that other apparatus, methods, or systems may be within the scope of the claims as interpreted by one of skill in the art.

The invention claimed is:

1. A face mask for filtering air, the face mask comprising:
   a face seal for providing an airtight flexible seal around the nose and mouth of a user;
   a support sealably attached to the face seal, wherein the support has an open area that allows for passage of incoming air and outlet valves for expelling exhaled air;
   a front shell for removably attaching to the support, wherein the front shell has inlet holes for allowing the incoming air to pass through the open area of the support; and
   a filter for filtering particulate elements from air, wherein the filter is configured to be housed between the front shell and the support, and the face seal provides a direct connection between the filter and the user, and
   wherein the front shell includes a pair of shell attachment members located at a sides of the front shell, and wherein the support includes a pair of inner attachment members that removably connect to the shell attachment members, and
   wherein the front shell includes a top shell connector located at a nose position of the front shell, and wherein the support includes an upper attachment member that hingedly connects with the top shell connector.

2. The face mask of claim 1, wherein the support comprises a framework that defines the open area.

3. The face mask of claim 2, wherein the framework comprises a central longitudinal frame member and at least two transverse frame members.

4. The face mask of claim 1, wherein the shell attachment members include an external release for disengaging the shell attachment member from the inner attachment member and thereby opening the face mask like a clam shell.

5. The face mask of claim 1, wherein the face seal is silicone.

6. The face mask of claim 1, wherein the front shell includes filter registration members located on an inside surface of the front shell for aligning the filter within the face mask.

7. The face mask of claim 1, wherein the front shell includes a number of stand-offs on an inside surface of the front shell adjacent to the inlet holes, for holding the filter off of the inner surface of the front shell.

8. A face mask for filtering air, the face mask comprising:
   a face seal for providing an airtight flexible seal around the nose and mouth of a user:
   a support sealably attached to the face seal, wherein the support has an open area that allows for passage of incoming air and outlet valves for expelling exhaled air;
   a front shell for removably attaching to the support, wherein the front shell has inlet holes for allowing the incoming air to pass through the open area of the support; and
   a filter for filtering particulate elements from air, wherein the filter is configured to be housed between the front shell and the support, and the face seal provides a direct connection between the filter and the user, and
   wherein the face seal is overmolded to the support such that the face seal seals the perimeter of the filter between the support and the front shell,
   wherein the filter is configured to be flat when not assembled and be curved to become a three dimensional form for insertion on to the support, and
   wherein the filter includes a pair of nose portions separated by a central nose slit, and wherein the nose portions mate together to form the three dimensional form when the filter is housed between the front shell and the support.

9. The face mask of claim 8, wherein the face seal includes a nose seal extending along a central longitudinal frame member of the support, wherein the nose seal includes a connector post connected to a post hole in the central longitudinal frame member, and wherein the nose seal is positioned to seal the nose portions of the filter to provide an airtight seal between the filter and the support.

10. The face mask of claim 8, wherein the support comprises a framework that defines the open area.

11. The face mask of claim 8, wherein the framework comprises a central longitudinal frame member and at least two transverse frame members.

12. The face mask of claim 8, wherein the shell attachment members include an external release for disengaging the shell attachment member from the inner attachment member and thereby opening the face mask like a clam shell.

13. The face mask of claim 8, wherein the face seal is silicone.

14. The face mask of claim 8, wherein the front shell includes filter registration members located on an inside surface of the front shell for aligning the filter within the face mask.

15. The face mask of claim 8, wherein the front shell includes a number of stand-offs on an inside surface of the front shell adjacent to the inlet holes, for holding the filter off of the inner surface of the front shell.

\* \* \* \* \*